US009402586B2

(12) United States Patent
Tsujii

(10) Patent No.: US 9,402,586 B2
(45) Date of Patent: Aug. 2, 2016

(54) STEREO X-RAY IMAGING APPARATUS AND STEREO X-RAY IMAGING METHOD

(71) Applicant: CANON KABUSHIKI KAISHA, Tokyo (JP)

(72) Inventor: Osamu Tsujii, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 151 days.

(21) Appl. No.: 13/685,328

(22) Filed: Nov. 26, 2012

(65) Prior Publication Data

US 2013/0163719 A1 Jun. 27, 2013

(30) Foreign Application Priority Data

Dec. 21, 2011 (JP) .................................. 2011-279977

(51) Int. Cl.
*A61B 6/02* (2006.01)
*G03B 35/00* (2006.01)
*A61B 6/06* (2006.01)
*A61B 6/00* (2006.01)

(52) U.S. Cl.
CPC . *A61B 6/022* (2013.01); *A61B 6/06* (2013.01); *A61B 6/463* (2013.01); *A61B 6/5235* (2013.01); *A61B 6/542* (2013.01); *A61B 6/545* (2013.01); *G03B 35/00* (2013.01); *Y02P 70/521* (2015.11)

(58) Field of Classification Search
CPC ...... A61B 6/022; A61B 6/4007; A61B 6/463; A61B 4/5235
USPC ............................................................ 378/41
See application file for complete search history.

(56) References Cited

U.S. PATENT DOCUMENTS

| 7,315,606 B2 | 1/2008 | Tsujii ............................... 378/20 |
| 7,386,157 B2 | 6/2008 | Tago et al. .................... 382/130 |
| 7,564,998 B2 | 7/2009 | Tsujii ............................. 382/128 |
| 7,873,146 B2 | 1/2011 | Okunuki et al. ............... 378/122 |
| 7,945,015 B2 | 5/2011 | Tsujii et al. ...................... 378/26 |
| 7,970,100 B2 | 6/2011 | Tsujii et al. ...................... 378/37 |
| 7,991,120 B2 | 8/2011 | Okunuki et al. ............... 378/124 |
| 2003/0081720 A1* | 5/2003 | Swift ....................... G01N 23/04 378/41 |

(Continued)

FOREIGN PATENT DOCUMENTS

| CN | 101505660 | 8/2009 |
| CN | 102209494 | 10/2011 |

(Continued)

OTHER PUBLICATIONS

Extended European Search Report dated Mar. 21, 2013 issued in counterpart EPA 12196443.1.

(Continued)

*Primary Examiner* — Robert Kim
*Assistant Examiner* — Eliza Osenbaugh-Stewar
(74) *Attorney, Agent, or Firm* — Fitzpatrick, Cella, Harper & Scinto

(57) ABSTRACT

Provided is a stereo imaging apparatus that generates X-rays from a plurality of different focal positions and that acquires a plurality of X-ray images from an X-ray detector, the stereo imaging apparatus including X-ray generation controlling means for controlling irradiated areas of X-rays so that an irradiated area in a detection area of the X-ray detector based on X-rays applied from a first focal position is included in an irradiated area in the detection area based on X-rays applied from a second focal position.

26 Claims, 5 Drawing Sheets

(56) References Cited

U.S. PATENT DOCUMENTS

| | | | |
|---|---|---|---|
| 2007/0230655 A1* | 10/2007 | Erbel | A61B 6/022 378/41 |
| 2008/0137934 A1 | 6/2008 | Sakaguchi | 382/132 |
| 2009/0285355 A1 | 11/2009 | Brada et al. | 378/20 |
| 2010/0166140 A1 | 7/2010 | Proksa | 378/8 |
| 2010/0208865 A1 | 8/2010 | Sendai | 378/28 |
| 2010/0249647 A1* | 9/2010 | Nakayama | 600/567 |
| 2011/0026807 A1* | 2/2011 | Wang | 382/154 |
| 2011/0058727 A1 | 3/2011 | Tsujii | 378/132 |
| 2011/0075799 A1 | 3/2011 | Okada et al. | 378/41 |
| 2011/0182492 A1 | 7/2011 | Grass | 372/131 |
| 2011/0216884 A1 | 9/2011 | Tsujii et al. | 378/62 |
| 2012/0162775 A1* | 6/2012 | Francois et al. | 359/630 |
| 2013/0003927 A1 | 1/2013 | Tsujii | 378/62 |
| 2013/0197342 A1 | 8/2013 | Tsujii | 600/407 |
| 2013/0243156 A1 | 9/2013 | Tsukamoto et al. | 378/62 |
| 2013/0294582 A1 | 11/2013 | Tsujii et al. | 378/150 |

FOREIGN PATENT DOCUMENTS

| | | |
|---|---|---|
| JP | 60-127698 | 7/1985 |
| JP | 6-319729 | 11/1994 |
| JP | 8-130752 | 5/1996 |
| JP | H09-224927 | 9/1997 |
| JP | 9-313471 | 12/1997 |
| JP | 10-146330 | 6/1998 |
| JP | 2008-142543 | 6/2008 |
| JP | 4411011 B2 | 2/2009 |
| JP | 2010-115270 | 5/2010 |
| JP | 2012-61197 | 3/2012 |
| JP | 2012-505009 | 3/2012 |

OTHER PUBLICATIONS

Office Action issued on Jul. 7, 2014, in counterpart Chinese patent application 201210557303.4, with translation.

Office Action issued on May 15, 2015, in counterpart Chinese patent application 201210557303.4, with translation.

F. Wang et al., "Visual Fatigue and Mitigation for Stereoscopic Image Observation", *Journal of Engineering Graphics*, No. 4, pp. 80-83 (2011); in Chinese, with English abstract.

JPO Office Action issued on Oct. 6, 2015 in counterpart Japanese patent application 2011-279977 (with translation).

* cited by examiner

__ US 9,402,586 B2 __

STEREO X-RAY IMAGING APPARATUS AND STEREO X-RAY IMAGING METHOD

BACKGROUND OF THE INVENTION

1. Field of the Invention

The present disclosure relates to a stereo X-ray imaging apparatus and a stereo X-ray imaging method. More specifically, the present invention relates to a stereo X-ray imaging apparatus and a stereo X-ray imaging method capable of applying X-rays to an object from a plurality of directions to take X-ray images to stereoscopically display the plurality of taken X-ray images.

2. Description of the Related Art

A stereo X-ray imaging apparatus has an advantage that an anteroposterior relationship between a plurality of blood vessels can be recognized.

However, a conventional X-ray limiting apparatus cannot limit the inside of two X-ray cones in stereoscopic imaging of a necessary region of an object. Therefore, there is a problem that unnecessary X-rays are provided to the object. Particularly, left and right edges of the application of X-rays do not match, and there is a problem that the exposure dose of X-rays of the object increases. Consequently, Japanese Patent Application Laid-Open No. S60-127698 discloses a configuration of using a limit to bring the left and right edges of the application of X-rays into line to thereby reduce the exposure dose.

Japanese Patent Application Laid-Open No. 2010-115270 discloses a technique related to a multi X-ray apparatus, in which the directions of X-rays can be changed. Specifically, the X-ray imaging apparatus of Japanese Patent Application Laid-Open No. 2010-115270 includes: two-dimensionally formed multi X-ray source and a plurality of limiting holes through which X-rays pass; and a collimator that can adjust sizes and positions of the plurality of limiting holes. In a first control mode, to translate an observed area when the X-ray source is changed, a control unit controls the sizes and the positions of the plurality of limiting holes so that the observed directions after the change and before the change are parallel. In a second control mode, to rotate the observed direction when the X-ray source is changed, the control unit controls the sizes and the positions of the plurality of limiting holes so that the centers of the observed areas are the same after the change and before the change.

Japanese Patent Application Laid-Open No. H06-319729 discloses a technique related to an X-ray apparatus for irradiation from a plurality of directions. In this way, X-rays are applied from two directions in the stereo X-ray imaging, and therefore, the exposure of the patient is greater than that in imaging from a single direction.

SUMMARY OF THE INVENTION

According to some embodiments of the present invention, provided is a stereo imaging apparatus that generates X-rays from a plurality of different focal positions and that acquires a plurality of X-ray images from an X-ray detector, the stereo imaging apparatus including X-ray generation controlling means for controlling irradiated areas of X-rays so that an irradiated area in a detection area of the X-ray detector based on X-rays applied from a first focal position is included in an irradiated area in the detection area based on X-rays applied from a second focal position.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

(First Embodiment)

Figure 1:
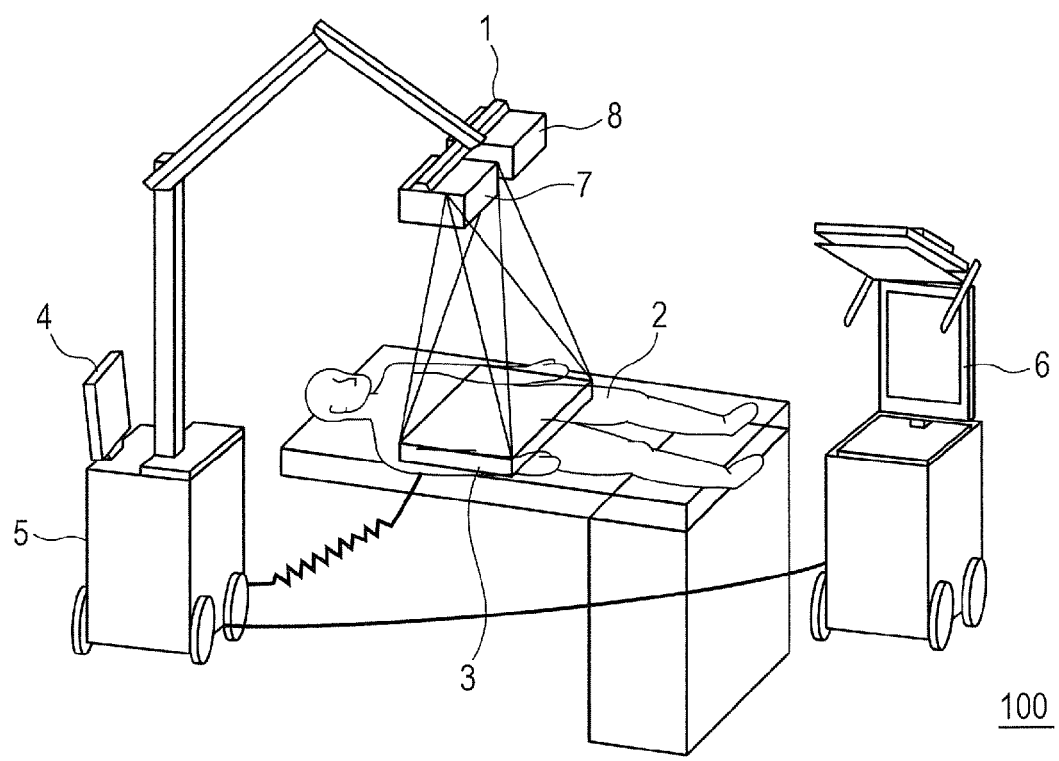
FIG. 1 is a diagram schematically illustrating a configuration of main parts of a stereo X-ray imaging apparatus according to a first embodiment of the present invention.

FIG. 1 is a diagram illustrating a configuration of main parts of a stereo X-ray imaging apparatus 100 according to a first embodiment of the present invention. Although the stereo X-ray imaging apparatus 100 is transportable in FIG. 1, the stereo X-ray imaging apparatus 100 may be stationary. As illustrated in FIG. 1, the stereo X-ray imaging apparatus 100 includes a stereo X-ray generating unit 1, an X-ray limiting unit 9 (see FIGS. 2A and 2B), an X-ray detector 3, a stereo display unit 6, an operating unit 4, and a control unit 5. The stereo X-ray generating unit 1 includes a first X-ray focal point 7 and a second X-ray focal point 8 as a plurality of X-ray focal points for applying X-rays. The first X-ray focal point 7 and the second X-ray focal point 8 alternately apply the X-rays. The X-ray limiting unit 9 can limit the X-rays applied from the first X-ray focal point 7 and the second X-ray focal point 8 to set an irradiated area of X-rays by the first X-ray focal point 7 and an irradiated area of X-rays by the second X-ray focal point 8 (see FIGS. 2A and 2B). Specific setting of the irradiated areas of X-rays by the X-ray limiter will be described later. For the convenience of the description, the irradiated area of X-rays by the first X-ray focal point 7 will be called a "first X-ray irradiated area 11", and the irradiated area of X-rays by the second X-ray focal point 8 will be called a "second X-ray irradiated area 12". The X-rays applied by the stereo X-ray generating unit 1 transmit through an object P (for example, a patient) and reach the X-ray detector 3. The X-ray detector 3 converts the X-rays transmitted through the object P and reached the X-ray detector 3 to electric signals. The control unit 5 applies image processing to the electric signals converted by the X-ray detector 3 to generate X-ray images. The X-ray detector 3 and the control unit 5 convert the X-rays applied from the first X-ray focal point 7 and transmitted through the object P and the X-rays applied from the second X-ray focal point 8 and transmitted through the object P to electric signals to generate X-ray images. More specifically, the control unit 5 generates an X-ray image (hereinafter, called a "first X-ray image 21") based on the X-rays applied from the first X-ray focal point 7 and an X-ray image (hereinafter, called a "second X-ray image 22") based on the X-rays applied from the second X-ray focal point 8. The stereo display unit 6 stereoscopically displays the generated X-ray images. More specifically, the stereo display unit 6 uses the first X-ray image 21 and the second X-ray image 22 to perform the stereoscopic display. It is only necessary that the stereo display unit can display stereo images, and various conventionally known stereo display apparatuses can be applied. An observer (user) uses the operating unit 4 to operate the stereo X-ray imaging apparatus 100. More specifically, the observer operates the stereo X-ray generating unit 1, the X-ray limiting unit 9, the X-ray detector 3, and the stereo display unit 6 through the operating unit 4.

Figure 2A:
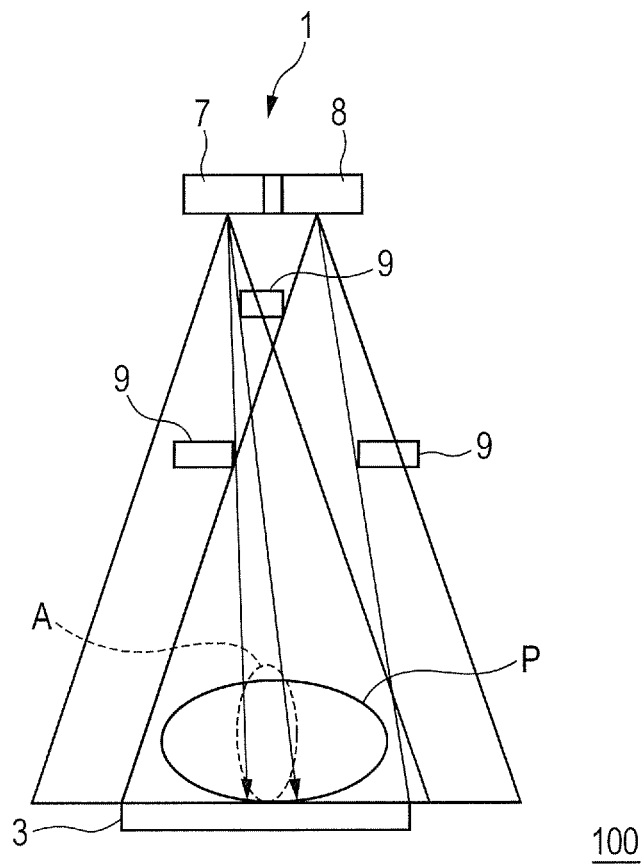
FIG. 2A is a diagram illustrating a relationship between X-rays applied from a first X-ray focal point and a second X-ray focal point, an X-ray limiter, and an area of interest of an object according to the present invention.
Figure 2B:
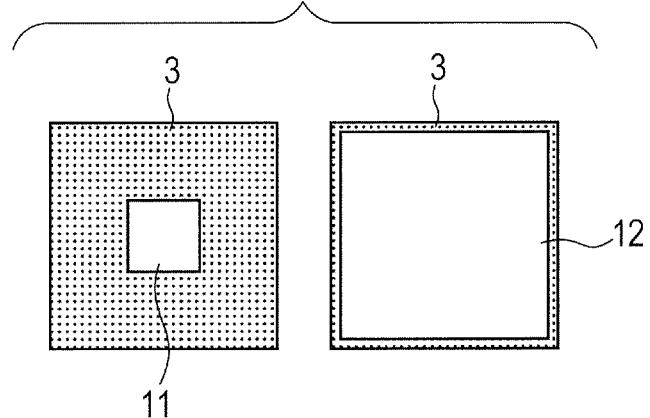
FIG. 2B is a diagram illustrating irradiated areas of X-rays to an X-ray detector according to the present invention.

FIGS. 2A and 2B are diagrams schematically illustrating irradiated areas of X-rays by the stereo X-ray imaging apparatus 100. FIG. 2A is a diagram illustrating a relationship between the X-rays applied from the first X-ray focal point 7 and the second X-ray focal point 8, the X-ray limiting unit 9, and an area of interest A of the object P. FIG. 2B is a diagram illustrating X-rays applied to the X-ray detector 3. The area of interest A here denotes a region that is a measurement target and that is subject to stereo X-ray imaging. As illustrated in FIGS. 2A and 2B, the second X-ray focal point 8 applies X-rays to a wide range including the area of interest A. The "wide range including the area of interest A" denotes a range that allows determining at which position of the object P the area of interest A is. Meanwhile, the first X-ray focal point 7 applies X-rays to the area of interest A (including a minimum range necessary to image the area of interest A, the same applies hereinafter). In this way, the first X-ray irradiated area 11 is smaller than the second X-ray irradiated area 12 and is included in the second X-ray irradiated area 12. As particularly illustrated in FIG. 2A, the X-ray limiting unit 9 sets the first X-ray irradiated area 11 and the second X-ray irradiated area 12 as described above.

The X-ray detector 3 converts the X-rays applied from the first X-ray focal point 7 and the X-rays applied from the second X-ray focal point 8 to electric signals. The control unit 5 applies image processing to the converted electric signals. The control unit 5 generates the first X-ray image 21 and the second X-ray image 22. The stereo display unit 6 uses the first X-ray image 21 and the second X-ray image 22 to perform stereoscopic display. In other words, the stereo display unit 6 displays a stereo X-ray image formed by the first X-ray image 21 and the second X-ray image 22.

According to the configuration, X-rays are applied to the area of interest A from both the first X-ray focal point 7 and the second X-ray focal point 8. Therefore, a stereo X-ray image can be obtained for the area of interest A. An X-ray image of a wide range including the area of interest A can be obtained by the X-rays applied from the second X-ray focal point 8. Therefore, the area of interest A can be stereoscopically displayed, while the wide range including the area of interest A of the object P is visualized by the X-rays. Therefore, the observer can observe the area of interest A by stereo X-ray images and can easily figure out at which region of the object P the area of interest A is.

Figure 3A:
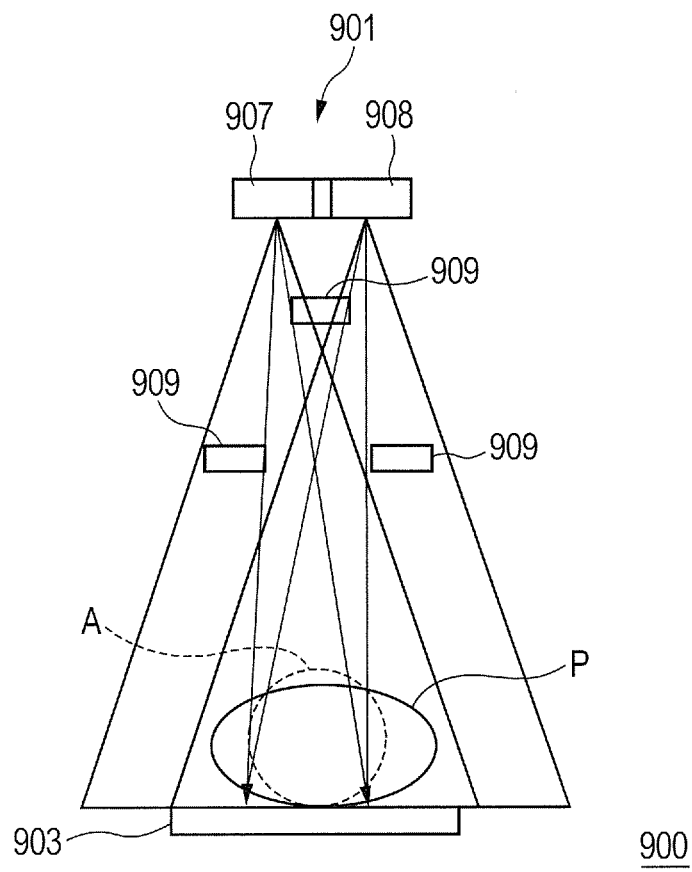
FIG. 3A is a diagram illustrating a relationship between X-rays applied from a first X-ray focal point and a second X-ray focal point, an X-ray limiter, and an area of interest of an object according to a conventional configuration.
Figure 3B:
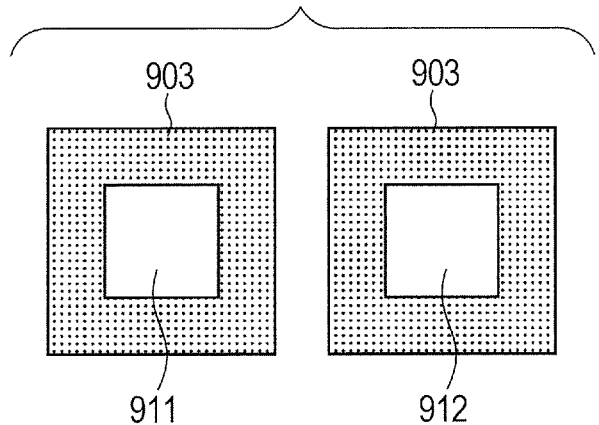
FIG. 3B is a diagram illustrating irradiated areas of X-rays to an X-ray detector according to the conventional configuration.

Effects of the first embodiment of the present invention will be described in comparison with a conventional example. FIGS. 3A and 3B are diagrams schematically illustrating a configuration of a conventional stereo X-ray imaging apparatus 900. FIG. 3A is a diagram illustrating a relationship between X-rays applied from a first X-ray focal point 907 and a second X-ray focal point 908 of a stereo X-ray generating unit 901, an X-ray limiting unit 909, and the area of interest A of the object P. FIG. 3B is a diagram illustrating irradiated areas of X-rays to the X-ray detector 3. As illustrated in FIGS. 3A and 3B, the X-ray limiting unit 909 causes the X-rays applied from the first X-ray focal point 907 and the second X-ray focal point 908 to irradiate the area of interest A of the object P in the conventional stereo X-ray imaging. According to the configuration, when the area of interest A is small compared to the size of the entire object P, it may be difficult to determine which region of the object P is imaged to obtain the stereo X-ray image. To solve the problem, there is a configuration of applying X-rays to a wide range including the area of interest A to obtain X-ray images. However, according to the configuration, X-rays need to be applied from both the first X-ray focal point 907 and the second X-ray focal point 908 to a region that is not the area of interest A. Therefore, the exposure dose of X-rays of the object P increases.

On the other hand, X-rays are applied to a region other than the area of interest A only from the second X-ray focal point 8 in the first embodiment of the present invention, and X-rays are not applied from the first X-ray focal point 7. Therefore, the overall exposure dose of the object P can be reduced. X-rays are applied to the area of interest A from both the second X-ray focal point 8 and the first X-ray focal point 7, and therefore, a stereo X-ray image can be obtained. This allows the observer to stereoscopically view the area of interest A. For a region around the area of interest A, an X-ray image can be obtained by X-rays from the second X-ray focal point 8. Therefore, a wide range including the area of interest A is visualized, and the position of the area of interest A can be easily figured out.

Figure 4A:
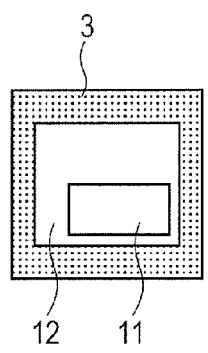
FIG. 4A is a plan view schematically illustrating a first X-ray irradiated area and a second X-ray irradiated area according to the first embodiment of the present invention.
Figure 4B:
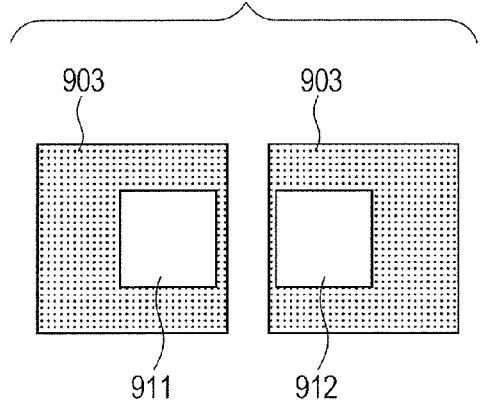
FIG. 4B is a plan view schematically illustrating a first X-ray irradiated area and a second X-ray irradiated area in an example that is not an embodiment of the present invention.
Figure 4C:
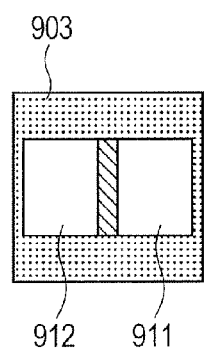
FIG. 4C is a plan view schematically illustrating the first X-ray irradiated area and the second X-ray irradiated area in the example that is not an embodiment of the present invention.

The first X-ray irradiated area 11 and the second X-ray irradiated area 12 will be described with reference to FIGS. 4A to 4C. FIGS. 4A to 4C are plan views schematically illustrating the first X-ray irradiated area and the second X-ray irradiated area 12. FIG. 4A illustrates the first embodiment of the present invention, and FIGS. 4B and 4C illustrate an example that is not an embodiment of the present invention. FIG. 4B separately depicts the first X-ray irradiated area 11 and the second X-ray irradiated area 12, and FIG. 4C depicts the first X-ray irradiated area 11 and the second X-ray irradiated area 12 on top of each other. As illustrated in FIG. 4A, the X-ray limiting unit 9 sets the first X-ray irradiated area 11 to be included in the second X-ray irradiated area 12. More specifically, the X-ray limiting unit 9 sets the first X-ray irradiated area 11 smaller than the second X-ray irradiated area 12.

Unlike in the configuration illustrated in FIGS. 4B and 4C, the first X-ray irradiated area 11 is not set to stick out from the second X-ray irradiated area 12 in the first embodiment of the present invention, as illustrated in FIG. 4A. Areas that can be stereoscopically viewed using the obtained X-ray images are areas where the first X-ray irradiated areas 11 and 911 and the second X-ray irradiated areas 12 and 912 overlap. Therefore, in the configuration illustrated in FIGS. 4B and 4C, the area that can be stereoscopically viewed is part of the first X-ray irradiated area 911 and the second X-ray irradiated area 912

(hatched area in FIG. 4C). Therefore, the section that can be stereoscopically viewed is smaller than in the configuration in which the second X-ray irradiated area 12 includes the first X-ray irradiated area 11, and the diagnostic performance of the object P cannot be improved. On the other hand, in the first embodiment of the present invention, the first X-ray irradiated area 11 is set to be included in the second X-ray irradiated area 12 as illustrated in FIG. 4A. According to the configuration, the entire first X-ray irradiated area 11 can be stereoscopically viewed.

Figure 5A:
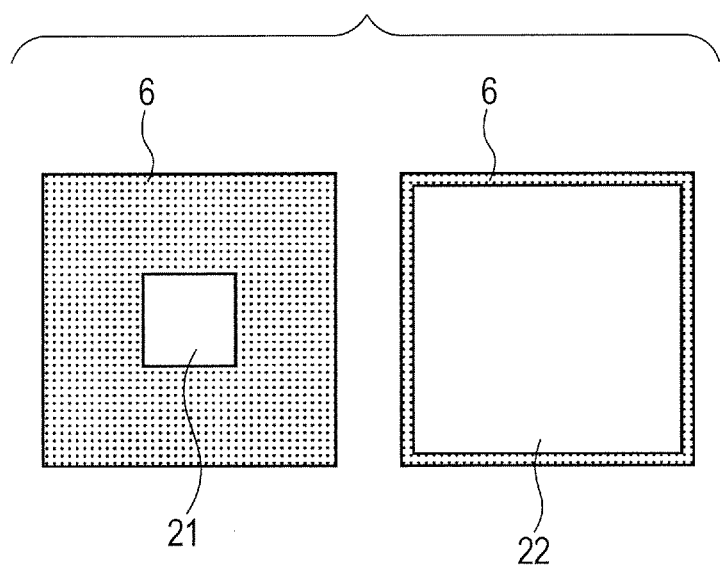
FIG. 5A is a diagram illustrating an X-ray image when a configuration for reducing eye fatigue of an observer is not applied.
Figure 5B:
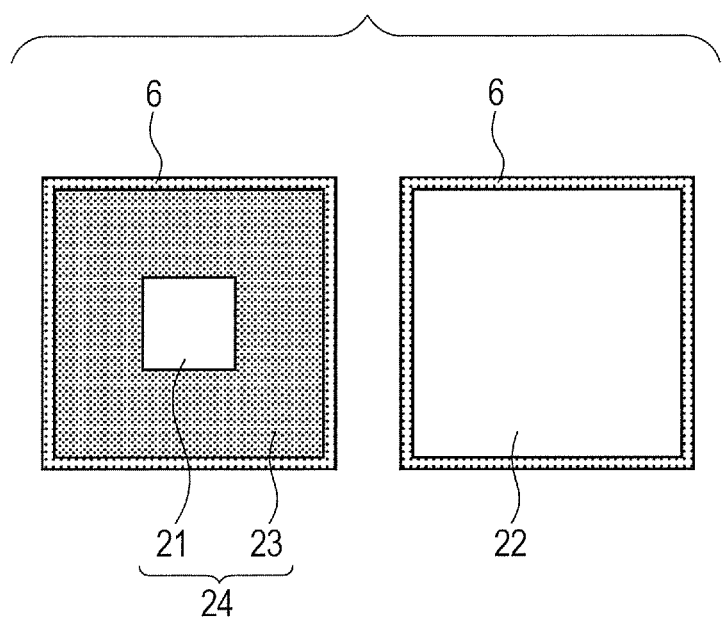
FIG. 5B is a diagram illustrating an X-ray image when the configuration for reducing eye fatigue of an observer is applied.

A configuration for reducing eye fatigue of the observer will be described with reference to FIGS. 5A and 5B. FIGS. 5A and 5B are diagrams schematically illustrating X-ray images displayed on the stereo display unit 6 and are diagrams separately depicting images entering left and right eyes. FIG. 5A illustrates X-ray images when the configuration for reducing the eye fatigue of the observer is not applied. FIG. 5B illustrates X-ray images when the configuration for reducing the eye fatigue of the observer is applied. The eyes of the observer may become easily tired if the first X-ray image 21 and the second X-ray image 22 are used for the stereoscopic display. The reason is that the sizes of the first X-ray image 21 and the second X-ray image 22 are different as illustrated in FIG. 5A, and the amounts of light entering the left and right eyes of the observer are different. The eyes of the observer more easily become tired with an increase in the difference between the sizes of the first X-ray image 21 and the second X-ray image 22.

Therefore, the control unit 5 creates an image by adding a predetermined complementary image 23 around the first X-ray image 21 as illustrated in FIG. 5B. The image provided with the complementary image 23 will be called a complemented image 24. The stereo display unit 6 uses the complemented image 24 and the second X-ray image 22 to perform the stereoscopic display. Specifics are as follows.

The control unit 5 adds the second X-ray image 22, which serves as the complementary image 23, around the first X-ray image 21 (=image with the area of interest A). The image provided with the second X-ray image 22 is set as the complemented image 24. In other words, the control unit 5 replaces the section including the area of interest A in the second X-ray image 22 with the first X-ray image 21. The replaced image is set as the complemented image 24. The size and the brightness of the created complemented image 24 are substantially the same as those of the second X-ray image 22. Therefore, the sizes and the brightness of the X-ray images entering the left and right eyes of the observer can be substantially the same in the configuration of using the complemented image 24 and the second X-ray image 22 for the stereoscopic display. This can reduce the eye fatigue of the observer. According to the configuration, the complemented image 24 with substantially the same size and the brightness as those of the second X-ray image 22 can be easily created.

The following configuration is also possible. The control unit 5 calculates averaged brightness of sections other than the area of interest A (=sections outside of the area of interest A) for the second X-ray image 22. The control unit 5 creates the complementary image 23 including pixels with the same brightness as the calculated averaged brightness. The control unit 5 adds the complementary image 23 around the first X-ray image 21 to create the complemented image 24. The outside dimension of the complementary image 23 is substantially the same as that of the second X-ray image 22. Similar effects as described above can also be attained with the configuration.

In the generation of the complemented image 24 with a combination of the first X-ray image 21 and the second X-ray image 22, the control unit 5 can apply a blending process to boundary sections of the first X-ray image 21 and the second X-ray image 22. In this way, a comfortable image can be obtained even if there is a large difference between the boundary sections due to a difference in the parallax.

In another embodiment, the control unit 5 displays the images by providing frame lines to the boundary sections of the first X-ray image 21 and the second X-ray image 22 in the complemented image 24 and to sections corresponding to the boundary sections in the second X-ray image. In this way, even if the boundary sections cannot be easily recognized due to the combination, the radiologist can easily recognize the corresponding parts and can easily perform the stereoscopic observation.

(Second Embodiment)

A second embodiment of the present invention will be described. The second embodiment illustrates a configuration applied to imaging and display of moving images. The same components as in the first embodiment of the present invention are designated with the same reference numerals, and the description will not be repeated.

In the second embodiment, the first X-ray irradiated area 11 may be set (=setting of the area of interest A) by the operation of the X-ray limiting unit 9 by the observer or may be automatically set by the process of the control unit 5.

The configuration of automatically setting the first X-ray irradiated area 11 will be described. The control unit 5 includes an image processing unit that executes image processing, and the image processing unit executes the image processing to set the first X-ray irradiated area 11. Specifically, the second X-ray focal point 8 is used to take an X-ray image of a wide range including the area of interest A. The image processing unit of the control unit 5 detects a motion vector of the X-ray image of the second X-ray focal point 8 and executes a thinning process. The image processing unit of the control unit 5 sets, as the first X-ray irradiated area 11 (=the area of interest A), a line segment area in the X-ray image of the second X-ray focal point 8, the line segment area including a motion vector equal to or greater than a predetermined threshold and applied with the thinning process. An image obtained by deleting a noise component from an edge component is defined as a line segment image, and an area including the line segment image is defined as the line segment area. Various known methods, such as a block matching method and a gradient method, can be applied as the method of detecting the motion vector.

An object of the detection of the motion vector is, for example, to use the X-ray image to detect movement of a catheter in a blood vessel, movement of a contrast agent in blood vessels, and movement of a therapeutic instrument. Therefore, the "predetermined threshold value" of the motion vector is set to a value that allows detecting the movement. In this way, the "predetermined threshold value" is set on an as-needed basis and is not particularly limited.

Various known thinning processes, such as frequency filtering and unsharp masking, are applied for the thinning process. The thinning process is applied to a sharpened X-ray image.

An object of the sharpening process is to extract an edge section included in the X-ray image. The thinning process can be applied to the image applied with the sharpening process to remove minute noise components. The line segment area of the image applied with the thinning process can be set as the area of interest A to detect the tip of the catheter, the tip of the flow of the contrast agent, and the tip of the therapeutic instrument.

The area with the motion vector equal to or greater than the predetermined threshold value and the line segment area after the thinning process are determined by rectangular areas surrounding the sections. The determined rectangular areas are displayed on the operating unit 4. The operator can change the rectangular area.

The first X-ray irradiated area 11 set as the area of interest A can be a rectangular area with a side equal to or greater than 50 mm. It is difficult to attain the stereoscopic effect if the side of the area of interest A is not equal to or greater than 50 mm.

An overall flow of the second embodiment of the present invention will be described.

The stereo X-ray imaging apparatus 100 uses the second X-ray focal point 8 to take an X-ray image (=the second X-ray image 22) of a wide range including the area of interest A. Since the first X-ray image 21 does not exist at this point, the stereo display unit 6 displays only the second X-ray image 22. Therefore, the stereo display unit 6 displays the image without one of the signals of the left and right images for stereoscopic display. The stereo display unit 6 may be configured to display the second X-ray image 22 in place of the first X-ray image 21. More specifically, the stereo display unit 6 displays the images in a state in which the left and right signals for stereoscopic display are signals of the same images. According to the configuration, the images are not stereoscopically displayed because the same images enter the left and right eyes of the observer. However, the eye fatigue of the observer can be reduced.

The image processing unit of the control unit 5 executes the process described above to determine the area of interest A. The image processing unit of the control unit 5 sets a larger area of interest A. More specifically, the area of interest A set by the image processing unit of the control unit 5 is set to a range wider than a region intended to be observed (=originally intended area of interest A). Subsequently, the first X-ray focal point 7 applies X-rays to the set area of interest A, the X-ray detector 3 detects X-rays applied from the first X-ray focal point 7 and transmitted through the object P, and the control unit 5 generates the first X-ray image 21. The stereo display unit 6 uses the first X-ray image 21 and the second X-ray image 22 to perform the stereoscopic display. According to the configuration, the stereo display unit 6 can stereoscopically display the area of interest A.

To narrow down the area of interest A, the X-ray limiting unit 9 narrows down the first X-ray irradiated area 11 (=the area of interest A). The setting of including the first X-ray irradiated area 11 in the second X-ray irradiated area 12 is maintained even if the position, the size and the range of the first X-ray irradiated area 11 are changed to narrow down the area of interest A. The size of the second X-ray irradiated area 12 is maintained without being changed to facilitate recognizing the position and the range of the area of interest A.

As in the first embodiment, the complementary image 23 may be added to the first X-ray image 21 to create the complemented image 24, and the complemented image 24 may be used to perform the stereoscopic display. According to the configuration, the eye fatigue of the observer can be reduced.

Although the embodiments of the present invention have been described in detail, the embodiments are intended to illustrate examples for implementing the present invention. The embodiments should not be construed as limiting the technical scope of the present invention. The present invention can be implemented in various forms without departing from the technical concept and main features of the present invention.

For example, although the first X-ray focal point 7 and the second X-ray focal point 8 are included as a plurality of X-ray focal points, and the first X-ray irradiated area 11 is included in the second X-ray irradiated area 12 in the embodiments, the present invention is not limited to the configuration. The "first X-ray focal point 7" and the "second X-ray focal point 8" are just distinguished for the convenience of the description. In short, it is only necessary that the X-ray irradiated area of one of the X-ray focal points be included in the X-ray irradiated area of the other X-ray focal point.

Although the stereo X-ray imaging apparatus 100 includes the first X-ray focal point 7 and the second X-ray focal point 8 as a plurality of X-ray focal points in the embodiments, the number of X-ray focal points is not limited. The stereo X-ray imaging apparatus 100 may include three or more X-ray focal points and may selectively use two of the X-ray focal points to perform the stereo X-ray imaging and the stereoscopic display.

The embodiments of the present invention are techniques effective for a field of a stereo X-ray imaging apparatus and a stereo X-ray imaging method. The embodiments of the present invention can be used for X-ray diagnostic imaging of humans and animals.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-279977, filed Dec. 21, 2011, which is hereby incorporated by reference herein in its entirety.

What is claimed is:

1. An imaging apparatus for a moving image, comprising:
   an X-ray generation controller configured to control an X-ray generator to repeatedly irradiate a first area of an object;
   a receiver configured to receive, by using a signal from an X-ray detector, a first X-ray moving image corresponding to the irradiated first area; and
   a processor configured to cause a display unit to display a first image based on the received first X-ray moving image,
   wherein said processor is further configured to obtain information to set a second area of the object within the first area,
   wherein said X-ray generation controller is further configured to, in a case in which said processor sets the second area within the first area, control the X-ray generator to limit the irradiated area to the set second area,
   wherein said receiver is further configured to, in a case in which the irradiated area is limited to the second area, receive a second X-ray moving image corresponding to the set second area, and
   wherein said processor is further configured to, in a case in which said receiver receives the second X-ray moving image, cause the display unit to display the first image based on the first X-ray moving image and a second image based on the second X-ray moving image, said processor being further configured to cause display of the second image on an area in the first image, the area of the first image corresponding to the set second area, such that the displayed second image is surrounded by an area of the displayed first image.

2. The imaging apparatus according to claim 1,
wherein the imaging apparatus is a stereo imaging apparatus, and
wherein said processor is further configured to cause the display unit to stereoscopically display the second image and a combination image obtained from a combination of the first image and the second image.

3. The imaging apparatus according to claim 2, wherein said processor is further configured to cause the display unit to display a plurality of images obtained according to the control by said X-ray generation controller.

4. The imaging apparatus according to claim 3, wherein said processor is further configured to cause the display unit to display a third image obtained by replacing a section, which is in the first image and which corresponds to the second image, with the second image, and the first image next to each other.

5. The imaging apparatus according to claim 4, wherein the first image and the third image are displayed next to each other on the display unit for a stereoscopic view.

6. The imaging apparatus according to claim 3, wherein said processor is further configured to cause the display unit to display the second image stereoscopically based on the second X-ray moving image corresponding to the irradiated second area and to display, around the second image, a complementary image in substantially the same size as the first image based on the first X-ray moving image corresponding to the irradiated first area.

7. The imaging apparatus according to claim 6, wherein the complementary image is an image including pixels with averaged brightness of the first image.

8. The imaging apparatus according to claim 2, wherein the irradiated second area is a rectangular area with a side equal to or greater than 50 mm.

9. The imaging apparatus according to claim 2, wherein the X-ray generator includes a plurality of X-ray focal points for applying X-rays, and
the X-ray detector detects the X-rays emitted by the plurality of X-ray focal points and transmitted through an object, and
wherein the imaging apparatus further comprises a stereo display unit that stereoscopically displays the X-rays detected by the X-ray detector, and
an X-ray irradiated area based on one of the plurality of X-ray focal points is set to be included in another X-ray irradiated area based on another one of the plurality of X-ray focal points.

10. The imaging apparatus according to claim 2, further comprising:
a combining unit configured to combine the first image and the second image according to a relationship between the irradiated first area and the irradiated second area.

11. The imaging apparatus according to claim 10, wherein said combining unit is operable to combine the second image on an area of the first image corresponding to the irradiated second area so that the second image is surrounded by an area of the first image.

12. An imaging method for a moving image, the imaging method comprising:
controlling an X-ray generator to repeatedly irradiate a first area of an object;
receiving a first X-ray moving image corresponding to the irradiated first area by using a signal from an X-ray detector;
causing a display unit to display a first image based on the received first X-ray moving image;
setting a second area of the object within the first area;
controlling the X-ray generator to limit the irradiated area to the set second area in a case in which the second area is set within the first area;
receiving a second X-ray moving image corresponding to the set second area in a case in which the irradiated area is limited to the second area; and
causing the display unit to display the first image based on the first X-ray moving image and a second image based on the second X-ray moving image in a case in which the second X-ray moving image is received,
wherein the second image is displayed on an area in the first image, the area of the first image corresponding to the set second area, such that the displayed second image is surrounded by an area of the displayed first image.

13. The imaging method according to claim 12,
wherein the imaging method is a stereo imaging method, and
wherein the imaging method further comprises causing the display unit to stereoscopically display the second image and a combination image obtained from a combination of the first image and the second image.

14. The imaging method according to claim 13, further comprising:
combining the first image and the second image according to a relationship between the irradiated first area and the irradiated second area, to obtain the combination image.

15. An imaging control apparatus for controlling imaging an X-ray moving image by an X-ray detector and an X-ray source, comprising:
a setting unit configured to set an X-ray irradiated area to a first area;
a control unit configured to cause the X-ray source to irradiate the first area set by the setting unit;
an obtaining unit configured to obtain a first X-ray moving image corresponding to the irradiated first area by using a signal from the X-ray detector; and
a display controlling unit configured to cause a display unit to display a first image based on the first X-ray moving image,
wherein the setting unit changes the X-ray irradiated area to a second area surrounded by the first area,
wherein the obtaining unit obtains a second X-ray moving image corresponding to the second area by using a signal from the X-ray detector in a case in which the X-ray irradiated area is changed to the second area, and
wherein the display controlling unit causes the display unit to display the second image based on the second X-ray moving image obtained by the obtaining unit and the first image based on the first X-ray moving image obtained by the obtaining unit such that the second image is surrounded by the first image.

16. The imaging control apparatus according to claim 15,
wherein the imaging control apparatus is an imaging control apparatus for controlling of imaging a stereo image, and
wherein the display controlling unit causes the display unit to stereoscopically display the second image based on the second X-ray moving image obtained by the obtaining unit and a combination image obtained from a combination of the first image and the second image.

17. The imaging control apparatus according to claim 16, wherein the display controlling unit causes the display unit to display the second image stereoscopically based on the second X-ray moving image corresponding to the second area and to display, around the second image, a complementary image in substantially the same size as the first image based on the first X-ray moving image corresponding to the first area.

18. The imaging control apparatus according to claim 17, wherein the complementary image is an image including pixels with averaged brightness of the first image.

19. The imaging control apparatus according to claim 15, wherein the display controlling unit causes the display unit to display a plurality of images based on a plurality of X-ray moving images obtained by the obtaining unit by using a signal from the X-ray detector.

20. The imaging control apparatus according to claim 19, wherein the display controlling unit causes the display unit to display a third image obtained by replacing a section, which is in the first image and which corresponds to the second image, with the second image, and the first image.

21. The imaging control apparatus according to claim 20, wherein the display controlling unit causes the display unit to stereoscopically display the first image and the third image.

22. The imaging control apparatus according to claim 15, wherein the second area is a rectangular area with a side equal to or greater than 50 mm.

23. The imaging control apparatus according to claim 15, wherein the X-ray source includes a plurality of X-ray focal points for applying X-rays, and the X-ray detector detects the X-rays emitted by the plurality of X-ray focal points and transmitted through an object, wherein the setting unit sets an X-ray irradiated area based on one of the plurality of X-ray focal points so as to be included in another X-ray irradiated area based on another one of the plurality of X-ray focal points.

24. The imaging control apparatus according to claim 15, further comprising:

a combining unit configured to combine the first image and the second image according to a relationship between the first area and the second area.

25. The imaging control apparatus according to claim 24, wherein said combining unit is operable to combine the second image on an area of the first image corresponding to the second area so that the second image is surrounded by an area of the first image.

26. The imaging control apparatus according to claim 15, wherein the display controlling unit causes the display unit to display a third image obtained by replacing a section, which is in the first image and which corresponds to the second image, with the second image.

* * * * *